US006447656B1

(12) United States Patent
Wieczorek (10) Patent No.: US 6,447,656 B1
(45) Date of Patent: Sep. 10, 2002

(54) BIOSENSOR

(75) Inventor: Lech Wieczorek, New South Wales (AU)

(73) Assignee: Australian Membrane and Biotechnology Research Institute, New South Wales (AU)

(*) Notice: Subject to any disclaimer, the term of this patent is extended or adjusted under 35 U.S.C. 154(b) by 0 days.

(21) Appl. No.: 09/445,852

(22) PCT Filed: Jun. 4, 1998

(86) PCT No.: PCT/AU98/00423

§ 371 (c)(1),
(2), (4) Date: Aug. 1, 2000

(87) PCT Pub. No.: WO98/55854

PCT Pub. Date: Dec. 10, 1998

(30) Foreign Application Priority Data

Jun. 4, 1997 (AU) .............................. PO7171

(51) Int. Cl.$^7$ ...................... G01N 27/26; G01N 27/327; G01N 27/333
(52) U.S. Cl. ....................... 204/403; 204/418
(58) Field of Search ................. 204/403, 415, 204/418

(56) References Cited

U.S. PATENT DOCUMENTS

| 5,756,355 A | * | 5/1998 | Lang et al. | ............. | 435/7.21 |
| 5,801,428 A | | 9/1998 | Felde et al. | ............. | 257/414 |
| 5,874,047 A | | 2/1999 | Schoning et al. | ........ | 422/82.02 |

FOREIGN PATENT DOCUMENTS

| EP | 0 441 120 A2 | 8/1991 |
| EP | 0 813 058 A1 | 12/1997 |
| WO | 90/05910 | 5/1990 |
| WO | 92/17788 | 10/1992 |
| WO | WO-9407593 A1 * | 4/1994 |
| WO | 96/05512 | 2/1996 |
| WO | 97/01092 | 1/1997 |

OTHER PUBLICATIONS

Pandey et al, "Tetracyanoquinodimethane mediated glucose sensor based . . . ," Biosensors & Bioelectronics, vol. 10, pp. 669–674 (1995), month unknown.

* cited by examiner

*Primary Examiner*—T. Tung
*Assistant Examiner*—Alex Noguerola
(74) *Attorney, Agent, or Firm*—Nixon & Vanderhye (57) ABSTRACT

The present invention provides a membrane based biosensor. The biosensor includes an electrode and a passivating layer bound to the electrode. A lipid membrane incorporating ionophores, the conductivity of the membrane being dependent on the presence or absence of an analyte, is bound to the passivating layer in a manner such that an ionic reservoir exists between the membrane and the passivating layer. Reservoir spanning molecules spanning the ionic reservoir are also included. These molecules are covalently attached at one end to the membrane and at the other to the passivating layer. The incorporation of the passivating provides greater stability to the sensor.

25 Claims, 5 Drawing Sheets

C-16 compounds

DLP-C11, n = 10

DLP-C16, n = 15

Figure 5

MSLOH, R = OH

MSL4XB, R =

BIOSENSOR

This application claims priority under 35 U.S.C. 120 from PCT/AU98/00423, filed Jun. 4, 1998.

The present invention relates to an improved membrane based biosensor and to methods of improving the stability of membrane based biosensors.

Biosensors based on ion channels or ionophores contained within lipid membranes that are deposited onto conducting electrodes, where the ionophores are switched in the presence of analyte molecules have been described in International Patent Application Nos PCT/AU88/00273; PCT/AU89/00352; PCT/AU90/00025; and PCT/AU93/00509 (the disclosures of which are incorporated herein by way of reference). As these biosensors rely on changes in ion conduction through the membrane, usually mediated by an ionophore, it is important that there exists an ionic reservoir between the electrode and the lipid membrane. It is also important that the lipid membrane is at least in part linked to the reservoir and that the membrane is at least in part tethered to the conductive substrate. The stability of the substrate and the stability of the link between the reservoir and the substrate will influence the stability of the total membrane plus ionic reservoir system and thus the stability of the biosensor membrane.

The present inventors have now found that the stability of the biosensor membrane can be improved by incorporating a passivating layer between the reservoir region and the conducting substrate. This passivating layer serves to increase the bonding between the reservoir forming linkers and the conductive substrate as well as serving to protect the conductive substrate surface from corrosive or electrochemical effects of the aqueous solution. This would improve the stability of the biosensor both during storage and during the actual measurement of the biosensor response on addition of analyte containing sample. A reduction in the drift of the biosensor response during analyte addition is also obtained.

Generally, formation of the reservoir functionality onto conductive substrates is through binding of individual reservoir molecules with the substrate. The present inventors have determined that by introducing binding, passivating layer between the reservoir forming molecules and the electrode the stability of the whole membrane system is improved. There is also preferably binding between the molecules making up the passivating layer. This binding may include van der Waal's forces, hydrogen bonding forces, ionic interactions or covalent linkage. Furthermore, if a thin, passivating layer is formed between the reservoir and the conductive surface such that water and ions are restricted from interacting with the conductive substrate then corrosive effects such as electrochemical degradation are minimised and the stability of the membrane is improved. This thin passivating layer may be eletrically insulating in nature. The ionic reservoir, in this case, has a reduced contact with the conductive substrate directly and information about the ion flux into or out of the ionic reservoir can be obtained by a variety of electronic transient pulse techniques commonly used to measure the charging and discharging of resistor/capacitor circuits.

Additionally, by introducing this thin layer between the ionic reservoir and the conductive substrate, then the spacing and orientation of the ionic reservoir forming molecules is determined by the structure of the thin layer substance rather than by the surface crystal orientation of the underlying conductive substrate.

Accordingly in a first aspect the present invention consists in a membrane based biosensor, the biosensor including an electrode, a passivating layer bound to the electrode, a lipid membrane incorporating ionophores, the conductivity of the membrane being dependent on the presence or absence of an analyte, an ionic reservoir between the membrane and the passivating layer, and spanning molecules spanning the ionic reservoir the molecules being covalently attached at one end to the membrane and at the other to the passivating layer.

In a preferred embodiment the biosensor includes a plurality molecules of following general structure:

in which:

A is a hydrophobic group of between 2–50 methylene units in length;

B is a group which spans the ionic reservoir;

C is a group capable of hydrogen bonding, forming van der Waal's interactions, ionic bonding or covalent bonding with other molecules contained within the passivating layer; and D is a group which binds to the conducting substrate.

In a preferred embodiment A is a hydrocarbon group of between 2–50 methylene units long, a phytanyl group, an unsaturated hydrocarbon of between 2–50 methylene groups long, a membrane spanning lipid, an archaebacterial lipid, a lipid hydrocarbon group, or a gramicidin derivative. It is presently preferred that A is a hydrocarbon group or an unsaturated hydrocarbon group of between 8–26 methylene units long or a gramicidin derivative.

In another preferred embodiment B is an oligoethylene glycol of between 4 to 20 ethylene glycol units long. Alteratively B may be repeating subunits of oligoethylene glycol of between 2 and 6 ethylene glycol units, the subunits being linked together via ester, amide or other linkages. It is highly preferred that in this arrangement that the linkages do not promote hydrogen bonding between the groups spanning the reservoir. In this regard it is preferred that the linkages are tertiary amides. As will be appreciated it is also highly preferred that linkages resistant to hydolysis such as tertiary amides are used.

In a further preferred embodiment group C of the above embodiment includes a secondary amide capable of hydrogen bonding with other amides; a hydrocarbon group capable of forming van der Waals interactions with other hydrocarbon groups, or a polymerisable group.

In a still further preferred embodiment D is a thiol, disulfide, sulfide, phosphine, silane or carboxylate.

It is further preferred that the group C in the above embodiment consists in a saturated hydrocarbon group of between 2 to 50 methylene units long, more preferably 8 to 30 methylene units long.

In a preferred embodiment the biosensor includes a plurality molecules of following general structure:

in which C and D are as defined above.

As will be recognised in the biosensor of the present invention group A will be within and form part of the membrane, group B will span the ionic reservoir and groups C and D will be within and form part of the passivating layer.

Figure 1:
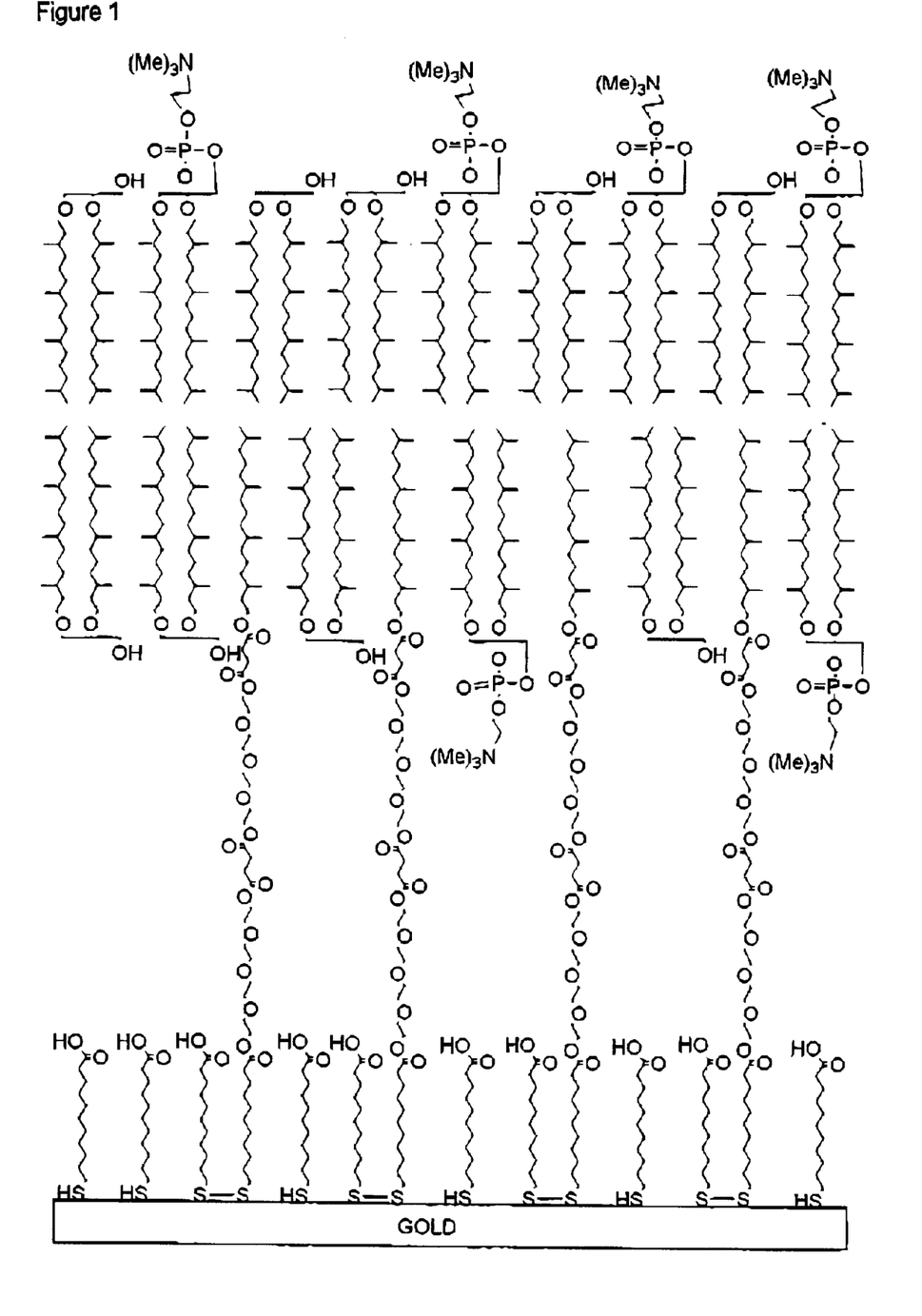
FIG. 1 is a schematic representation of part of the biosensor of the present invention.

In a preferred embodiment the biosensor has a structure as shown in FIG. 1.

In a further preferred embodiment the passivating layer has reduced permeability towards water and towards ions thus protecting the surface of the conductive substrate from destabilising effects due to water or ions.

In a preferred embodiment the biosensor includes a plurality molecules of following general structure:

A—B—C—D in which:

A is a hydrophobic group such as a hydrocarbon group of between 2–50 methylene units long, a phytanyl group, an unsaturated hydrocarbon of between 2–50 methylene groups long, a membrane spanning lipid or archaebacterial lipid analog, a lipid hydrocarbon group, or a gramicidin derivative;

B is a group which spans the ionic reservoir;

C is a group that inhibits the permeation of water or ions to the conductive surface; and D is a group capable of being attached to a conducting substrate such a a thiol, disulfide, sulfide, phosphine, silane, carboxylate or other group known to form strong interactions with surfaces.

In a preferred embodiment A is a hydrocarbon group or an unsaturated hydrocarbon group of between 8–26 methylene units long.

In another preferred embodiment B is an oligoethylene glycol of between 4 to 20 ethylene glycol units long. Alteratively B maybe repeating subunits of oligoethylene glycol of between 2 and 6 ethylene glycol units, the subunits being linked together via ester, amide or other linkages. It is highly preferred that in this arrangement that the linkages do not promote hydrogen bonding between the groups spanning the reservoir. In this regard it is preferred that the linkages are tertiary amides. As will be appreciated it is also highly preferred that linkages resistant to hydolysis such as tertiary amides are used.

In a further preferred embodiment group C includes a hydrocarbon group capable of forming van der Waals interactions with other hydrocarbon groups. The hydrocarbon group may contain a polymerisable group. Additionally the group may be functionalised at the distal end to the group D in order to modulate the function of the ion reservoir.

It is further preferred that the group C in the above embodiment comprises a saturated hydrocarbon group of between 2 to 50 methylene units long, more preferably between 8 to 30 methylene units long.

In a preferred embodiment the biosensor includes a plurality molecules of following general structure:

C—D in which C and D are as defined above.

In a yet another preferred embodiment the passivating layer is strongly bound to the conductive substrate and the functionality that make up the ionic reservoir.

Additionally it is preferred that the group C may be functionalised at the distal end to the group D. This modification may include the incorporation of hydrophilic or hydrophobic groups, amides, alcohols, acids, amines, acrylamide or acrylate or other polymerisable groups that may be used to further stabilise the passivating layer and may be used to modulate the ion reservoir function.

Figure 2:
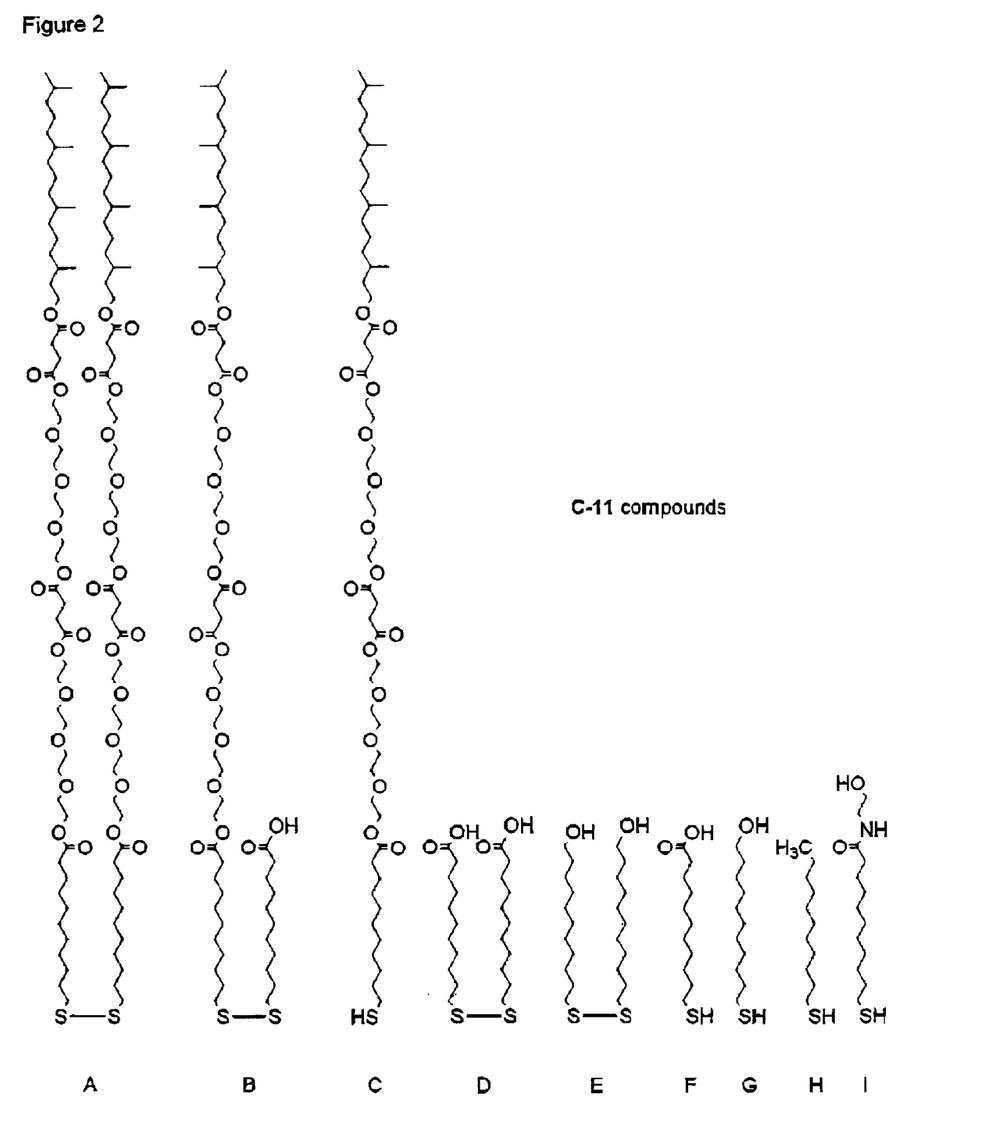
FIGS. 2 and 3 show structures of preferred compounds used in the present invention.

It is further preferred to use molecules such as those shown below and in FIGS. 2 and 3.

where:

n=8 to 16 m=1 to 10 p=1 to 10 k=0 to 10

R, $R_1$, $R_2$, $R_3$, $R_4$=independently H, methyl, ethyl

L=hydrocarbon such as a phytanyl chain, or other lipidic hydrocarbon

P=a thiol, disulfide, sulfide, or other group for attaching to metal surfaces such as gold, platinum, palladium, silver etc; or a silane or alkoxy silane or chloro silane for attaching to silica or metal oxide or other conductive surface as is known to those skilled in the art.

In a second aspect the present invention consists in a biosensor of any aspects one or two wherein the flux of ions mediated by an ionophore through the membrane into the ionic reservoir is measured by transient electrical pulse techniques.

In order that the nature of the present invention may now be more clearly understood preferred forms thereof will now be described with reference to following non-limiting examples and Figures, in which.

MATERIALS AND METHODS

ABBREVIATIONS

Figure 4:
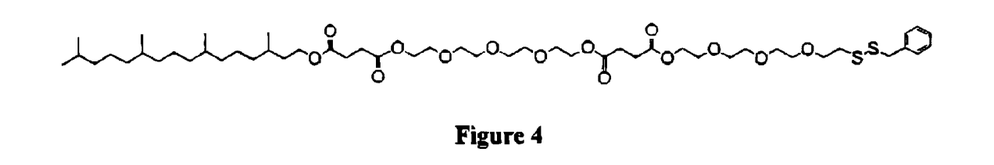
FIG. 4 shows the structure of DLP.
Figure 5:
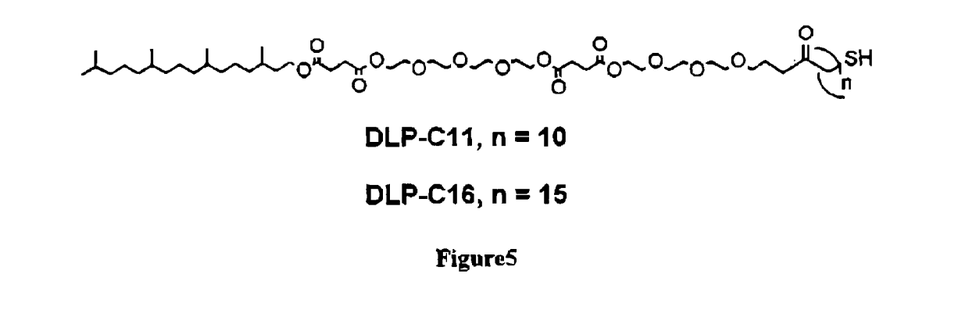
FIG. 5 shows the structures of DLP-C11 and DLP-C16.
Figure 6:
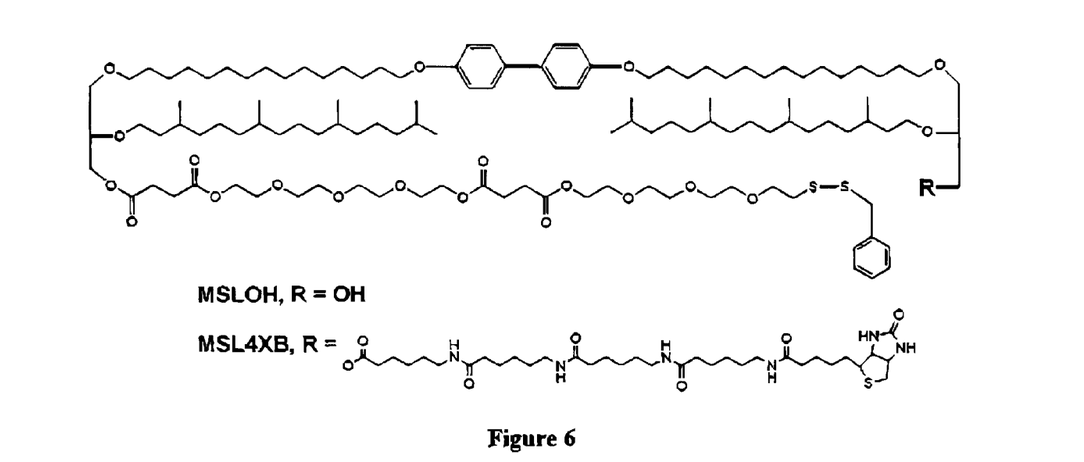
FIG. 6 shows the structures of MSLOH and MSL-4XB.
Figure 7:
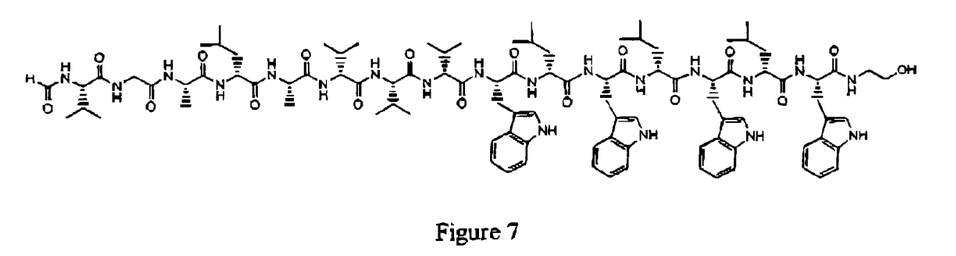
FIG. 7 shows the structure of gramicidin (gA)
Figure 8:
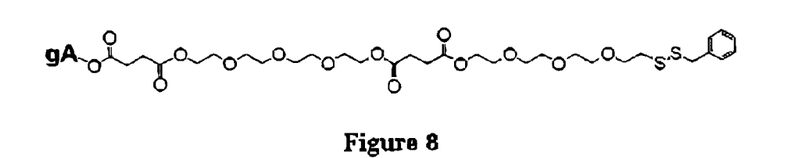
FIG. 8 shows the structure of gA-YY.
Figure 9:
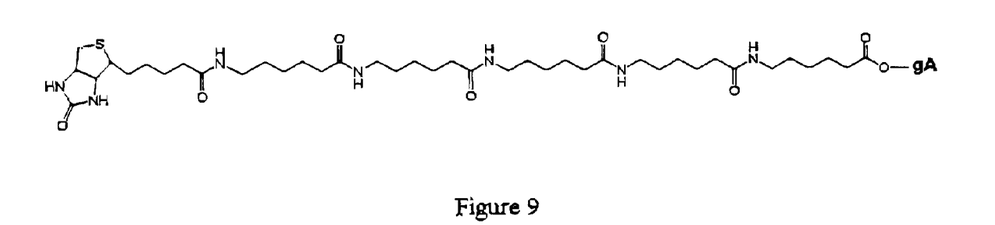
FIG. 9 shows the structure of gA-5XB

| | |
|---|---|
| DLP | 'Double length' phytanol, see FIG. 4 |
| PC lipid mixture | A mixture of 1,2-di(3RS,7R,11R-phytanyl)-glycero-3-phosphocholine and 1,2-di(3RS,7R,11R-phytanyl)glycerol in a 7:3 ratio |
| DLP-C11 | 'Double length' phytanol, attached to C11 foot, see FIG. 5 |
| DLP-C16 | 'Double length' phytanol, attached to C16 foot, see FIG. 5 |
| BnDS | Benzyl disulfide |
| MSLOH | 'Membrane spanning lipid', see FIG. 6 |
| MAAD | Mercaptoacetic acid disulfide |
| MSL-4XB | Biotinylated membrane spanning lipid, see FIG. 6 |
| gA | Gramicidin, see FIG. 7 |
| gA-YY | Tethered gramicidin, see FIG. 8 |
| DPEPC | 1,2-di(3RS,7R,11R-phytanyl)-glycero-3-phosphocholine |
| GDPE | 1,2-di(3RS,7R,11R-phytanyl)glycerol |
| gA-5XB | Biotinylated gramicidin, see FIG. 9 |

| ABBREVIATIONS | |
|---|---|
| DCC | Dicyclohexylcarbodimide |
| DMAP | Dimethylaminopyridine |

11-Mercaptoundecanoic acid (G)

11-Bromoundecanoic acid (20.0 g, 0.075 mol) and thiourea (6.3 g, 1.1 equiv.) were refluxed in ethanol (250 mL) overnight. Sodium hydroxide (6.3 g) in water (20 mL) was added and the mixture was further refluxed for 2 hr. The solution was cooled and acidified with 1N HCl. Ethanol was evaporated under reduced pressure and the aqueous residue was extracted With $CH_2Cl_2$. The combined organic extracts were dried ($MgSO_4$) and evaporated to give white powder. Yield: 15.0 g (91%)

$^1H$ $\delta(CDCl_3)$: 1.32 (m, 13H), 1.62 (m, 4H), 2.35 (t, 2H), 2.52 (m, 2H).

Undecanoic Acid Disulphide (D)

11-Mercaptoundecanoic acid (G) (3.0 g, 13.7 mmol) and triethylamine (4 mL, 2.1 equiv.) were dissolved in $CH_2Cl_2$/$CH_3OH$ (1:1) mixture (20 mL) and cooled. A solution of iodine in methanol was added until excess $I_2$ was present. The solvent was evaporated under reduced pressure and the residue was dissolved in $CH_2Cl_2$. The solution was acidified using 3N HCl and little methanol was added to dissolve insoluble solid. The organic phase was separated, dried ($MgSO_4$) and evaporated to yield a solid residue. The product was recrystallised once each from acetone and toluene. Yield: 1.2 g (40%)

$^1H$ $\delta(CDCl_3)$: 1.26 (br, 24H), 1.62 (br, 8H), 2.37 (t, 4H), 2.65 (m, 4H).

11-Mercaptoundecanol (H)

11-Mercaptoundecanoic acid (G) (1.0 g, 4.6 mmol) was dissolved in dry THF (20 mL) and borane dimethyl sulphide (3 mL, 1.1 equiv.) was slowly added under $N_2$ atmosphere. The mixture was stirred at room temperature for 4 hr. Water was added to the solution was extracted using ethyl acetate. The organic extract was washed with 1N HCl, water and saturated sodium bicarbonate solution successively. After drying ($MgSO_4$), the solvent was evaporated to give a clear oil. The crude oil was purified by column chromatography [eluant: hexane/ethyl acetate (8:2)]. Yield: 0.45 g (48%)

$^1H$ $\delta(CDCl_3)$: 1.28 (br, 18H), 1.58 (br, 4H), 2.52 (q, 2H), 3.65 (q, 2H).

Undecanol Disulphide (E)

11-undecanoic acid disulphide (D) (0.5 g, 4.6 mmol) was dissolved in dry THF (20 mL) and borane dimethyl sulphide (3 mL, 1.1 equiv.) was slowly added under $N_2$ atmosphere. The mixture was stirred at room temperature for 5 hr. Water was added to the solution was extracted using ethyl acetate. The organic extract was washed with 1N HCl, water and saturated sodium bicarbonate solution successively. After drying ($MgSO_4$), the solvent was evaporated to give a white powder. Yield: 0.15 g (32%)

$^1H$ $\delta(CDCl_3)$: 1.28 (br, 28H), 1.58 (br, 8H), 2.68 (t, 4H), 3.63 (t, 4H).

Compound (J)

Undecanoic acid disulphide (D) (0.43, 1.0 mmol) and succinic anhydride (0.23 g, 2.0 mmol) were dissolved in $CH_2Cl_2$ (30 mL). DMAP (20 mg, 0.1 equiv.) and DCC (0.41, 2.0 mmol) were added and the mixture was heated at 50° C. for 1 hr. The mixture was filtered and the filtrated was added with ethanolamine (1.5 equiv.). After stirring for further 2 hr. insoluble powder was collected and was purified by column chromatography [eluant: methanol/dichloromethane (1:9)].

Yield: 0.18 g (35%)

$^1H$ $\delta(CDCl_3)$: 1.38 (br, 24H), 1.68 (br, 8H), 2.22 (t, 4H), 2.71 (t, 4H), 3.31 (t, 4H), 3.62 (t, 4H).

63 mg (0.12 mmol) of the purified disulphide was dissolved in a ethanol/water mixture (20:3) (23 mL). Triphenylphosphine (47 mg, 1.5 equiv.) was added and the mixture was stirred at room temperature overnight. The solvent was evaporated under reduced pressure and the solid residue was purified by column chromatography [eluant: methanol/$CH_2Cl_2$ (8:92)]. Yield: 10 mg (16%)

$^1H$ $\delta(CDCl_3)$: 1.35 (br, 12H), 1.62 (br, 4H), 2.22 (t, 2H), 2.52 (t, 2H), 3.32 (t, 2H), 3.62 (t, 2H).

Phytanol (1)

Phytol (5.0 g, 16.7 mmol) was stirred in ethanol (50 mL) in the presence of Raney nickel (1.0 g, 50% slurry in water) overnight under $H_2$ atmosphere. The catalyst was filtered off and the solvent evaporated to give a clear oil. Yield: 4.9 g (97%)

$^1H$ $\delta(CDCl_3)$: 0.87 (m, 15H), 1.25 (br, 24H), 3.70 (br, 2H).

Phytanyl Succinate (2)

Phytanol (1) (5.0 g, 16.7 mmol) and succinic anhydride (2.5 g, 1.5 equiv.) were dissolved in pyridine (20 mL) and stirred at room temperature overnight. Pyridine was removed under reduced pressure and 0.5N HCl (100 mL) was added. The aqueous solution was extracted with $CH_2Cl_2$. The combined organic extracts were dried ($MgSO_4$) and evaporated to give an oil. The crude product was purified by column chromatography [eluant: ethyl acetate/hexane (15:85)]. Yield: 5.5 g (82%)

$^1H$ $\delta(CDCl_3)$: 0.87 (m, 15H), 1.25 (br, 24H), 2.65 (m, 4H), 4.18 (t, 2H).

Compound (3)

Phytanyl succinate (2) (4.2 g, 0.01 mol), tetraethylene glycol (10.2 g, 5 equiv.) and 4-dimethylaminopyridine (DMAP) (0.13 g, 0.1 equiv.) were dissolved in $CH_2Cl_2$ (50 mL). 1,3-Dicyclohexylcarbodiimide (DCC) (4.35 g, 2 equiv.) was added and the mixture was stirred at room temperature overnight. The solvent was evaporated and the residue was purified by column chromatography [eluant: ethyl acetate/hexane (6:4)]. Yield. 2.6 g (43%)

$^1H$ $\delta(CDCl_3)$: 0.85 (m, 15H), 1.25 (br, 24H), 2.65 (t, 4H), 3.67 (m, 14H), 4.12 (t, 2H), 4.27 (t, 2H).

Compound (4)

Compound (3) (142 g, 2.5 mmol) and succinic anhydride (0.37 g, 1.5 equiv.) were dissolved in pyridine (20 mL) and stirred at room temperature overnight. Pyridine was removed under reduced pressure and 1N HCl (50 mL) was added. The aqueous solution was extracted with ethyl acetate. The combined organic extracts were dried ($MgSO_4$) and evaporated to give an oil. The crude oil was purified by column chromatography [eluant: ethyl acetate/hexane (7:3)]. Yield: 1.4 g (84%)

$^1H$ $\delta(CDCl_3)$: 0.87 (m, 15H), 1.25 (br, 24H), 2.65 (m, 8H), 3.67 (m, 12H), 4.12 (t, 2H), 4.27 (t, 4H).

Compound (5)

Compound (4) (1.4 g, 2.0 mmol) and tetraethylene glycol (2.0 g, 5 equiv.) were dissolved in $CH_2Cl_2$ (30 mL). DMAP (30 mg, 0.1 equiv.) and DCC (0.9 g, 2 equiv.) were added and the mixture was stirred at room temperature overnight. The solution was filtered and then reduced under pressure. Water was added to the residue and extracted with $CH_2Cl_2$. The combined organic extracts were dried ($MgSO_4$) and evaporated to yield an oil. The crude oil was purified by column chromatography [eluant: methanol/dichloromethane (3:97)]. Yield: 1.1 g (62%)

$^1H$ $\delta(CDCl_3)$: 0.87 (m, 15H), 1.25 (br, 24), 2.62 (m, 8H), 3.65 (m, 26H), 4.12 (t, 2H), 4.26 (m, 6H).

Compound (B)

Compound (5) (0.91 g, 1.1 mmol) and undecanoic acid disulphide (D) (0.23 g, 0.53 mmol) were dissolved in $CH_2Cl_2$ (30 mL). DMAP (13 mg, 0.1 equiv.) and DCC (0.24 g, 1.1 equiv.) were added and the mixture was stirred at room temperature overnight. The solution was filtered and then reduced under pressure. The crude oil was purified by column chromatography [eluant; hexane/ethyl acetate (1:9)]. Yield: 0.25 g (18%)

$^1H$ $\delta(CDCl_3)$: 0.87 (m, 15H), 1.25 (br, 56H), 2.28 (t, 2H) 2.32 (t, 2H), 2.65 (m, 8H), 2.68 (t, 4H), 3.65 (m, 24H), 4.10 (m, 2H, 4.23 (m, 8H).

Compound (A)

Further elution [hexane/ethyl acetate (1:9)] from the column of (B) gave symmetrical disulphide (A) as the second product. Yield: 0.42 g (26%)

$^1H$ $\delta(CDCl_3)$: 0.87 (m, 30H), 1.25 (br, 80H), 2.32 (t, 4H), 2.65 (m, 16H), 2.68 (t, 4H), 3.65 (m, 48H), 4.11 (t, 4H), 4.25 (m, 16H).

Compound (C)

Compound (A) (0.1 g, 0.048 mmol) was dissolved in ethanol/water mixture (20:3) (23 mL), Triphenyl phosphine (0.03 g, 2.9 equiv.) was added and the mixture was stirred at room temperature for 3 days. The solvent was evaporated under reduced pressure and the residue was taken up in $CH_2Cl_2$. The organic solution was dried ($MgSO_4$) and evaporated. The crude product was purified by column chromatography [eluant: hexane/ethyl acetate (1:9)]. Yield: 49 mg (49%)

$^1H$ $\delta(CDCl_3)$: 0.87 (m, 15H), 1.25 (br, 24H), 2.32 (t, 2H), 2:52 (m, 2H), 2.68 (t, 8H), 3.65 (m, 24H), 4.12 (t, 2H), 4.25 (m, 8H).

16-Iodohexadecanoic Acid (6)

16-Hexadecanolide (5.0 g, 0.02 mol) was added to a mixture of HI (30 g) and acetic acid (20 g). The mixture was heated to 100° C. overnight. After cooling it was poured into a cold sodium thiosulphate solution (150 mL, 10%) and extracted using $CH_2Cl_2$. The combined organic extracts were dried ($MgSO_4$) and evaporated to give a white solid. The crude product was recrystallised from diethyl ether. Yield: 4.8 g (64%)

$^1H$ $\delta(CDCl_3)$: 1.28 (br, 22H), 1.65 (br, 2H), 1.85 (m, 2H), 2.35 (t, 2H), 3.18 (t, 2H).

16-Mercaptohexadecanoic Acid (N)

A mixture of 16-iodohexadecanoic acid (6) (4.0 g, 10.4 mmol) and thiourea (0.88 g, 1.1 equiv.) in ethanol (100 mL) was refluxed overnight under $N_2$ atmosphere. The solution was cooled to room temperature. Sodium hydroxide (1.0 g in 10 mL of water) wad added and the mixture was further heated for 2 hr. After cooling to room temperature 1N HCl was added and the product was extracted using $CH_2Cl_2$. The organic extract was dried and evaporated to give a white solid Yield: 2.1 g (69%)

$^1H$ $\delta(CDCl_3)$: 1.28 (br, 22H), 1.62 (br, 4H), 2.35 (t, 2H), 2.50 (t, 2H).

Hexadecanoic Acid Disulphide (M)

Method 1

16-Mercaptohexadecanoic acid (N) (1.5 g, 5.2 mmol) and triethylamine (1.5 mL, 2.1 equiv.) were dissolved in $CH_2Cl_2/CH_3OH$(1:1) mixture (20 mL) and cooled. A solution of methanol and iodine was added until excess $I_2$ was present. The solvent was evaporated under reduced pressure and the residue was dissolved in $CH_2Cl_2$. The solution was acidified using 3N HCl and little methanol was added to dissolve insoluble solid. The organic phase was separated, dried ($MgSO_4$) and evaporated to yield a solid residue. The product was recrystallised from acetone. Yield: 0.32 g (21%)

Method 2

A mixture of 16-iodohexadecanoic acid (6) (4.0 g, 10.4 mmol) and thiourea (0.88 g, 1.1 equiv.) in ethanol (100 mL) was refluxed overnight at room atmosphere. The solution was cooled to room temperature. Sodium hydroxide (1.0 g in 10 mL of water) wad added and the mixture was further heated for 2 hr. After cooling to room temperature 1N HCl was added and the insoluble product was collected by filtration. Yield: 2.2 g (73%)

$^1H$ $\delta(CDCl_3)$: 1.28 (br, 44H), 1.62 (br, 8H), 2.36 (t, 4H), 2.68 (t, 4H).

Figure 3:
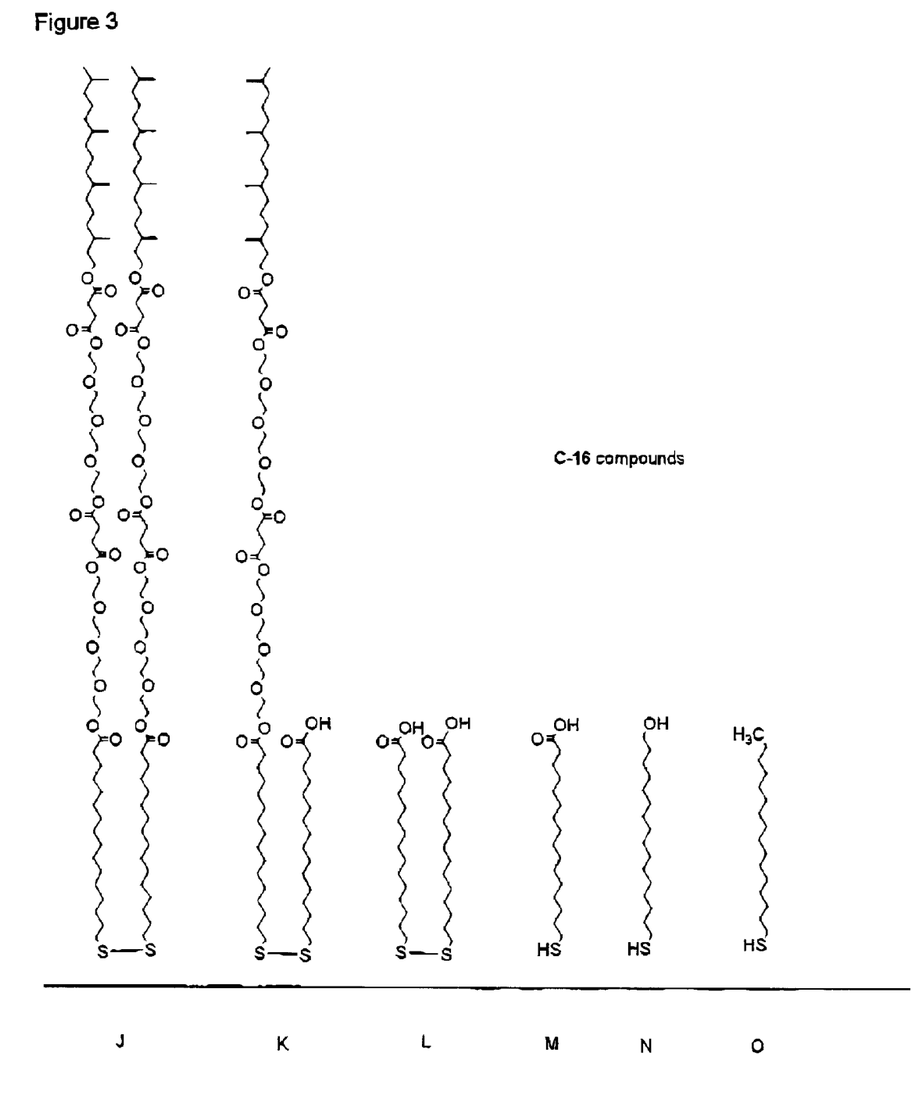

Compound (L) (FIG. 3)

Compound (5) (0.20 g, 0.23 mmol) and hexadecanoic acid disulphide (M) (0.12 g, 0.21 mmol) were dissolved in $CH_2Cl_2$ (20 mL). DMAP (5 mg, 0.1 equiv.) and DCC (53 mg, 1.1 equiv.) were added and the mixture was stirred at room temperature for 48 hr. The solution was filtered and then reduced under pressure. The crude oil was purified by column chromatography [eluant: hexane/ethyl acetate (15:85)]. Yield: 31 mg (10%)

$^1H$ $\delta(CDCl_3)$: 0.85 (m, 15H), 1.22 (br, 76H), 2.32 (t, 4H), 2.65 (m, 8H), 2.70 (t, 4H), 3.65 (m, 24H), 4.12 (m, 2H), 4.25 (m, 8).

Compound (K)

Further elution [hexane/ethyl acetate (1:9)] from the column of (L) gave symmetrical disulphide (K) as the second product. Yield: 0.42 g (26%)

16-Mercaptohexadecanol (O)

16-mercaptohexadecanoic acid (N) (0.2 g, 0.7 mmol) was dissolved in dry THF (20 mL) and borane dimethyl sulphide (1 mL, 1.1 equiv.) was slowly added under $N_2$ atmosphere. The mixture was stirred at room temperature for 4 hr. Water was added to the solution was extracted using ethyl acetate. The organic extract was washed with 1N HCl, water and saturated sodium bicarbonate solution successively. After drying ($MgSO_4$), the solvent was evaporated to give a white powder. Yield: 87 mg (46%)

$^1H$ $\delta(CDCl_3)$ 1.28 (br, 24H), 1.58 (br, 8H), 2.52 (q, 2H), 3.63 (t, 2H).

11-(Diphenylmethylthio)-undecanoic Acid

A solution of 11-mercaptoundecanoic acid (300 mg, 1.3 mmol) and diphenylmethanol (255 mg, 1.3 mmol) in trifluoroacetic acid was stirred at RT, under nitrogen for 30 min. Trifluoroacetic acid was evaporated under high vacuum, the residue dissolved in ether (20 ml), washed with water (3×20 ml), dried and evaporated. The residue was purified by chromatography (light pet—ethyl acetate, 80:20–50:50) on silica to give the desired product (220 mg, 42%), m.p. (Found C, 74.55; H, 8.77. $C_{24}H_{34}O_2S$ requires C, 74.96; H, 8.39) ms (EI) 384.

$^1$H nmr ($CDCl_3$) 1.22–1.29 (m, 12H, $CH_2$), 1.58 (m, 4H, $CH_2$), 2.34 (t, 2H, $CH_2$—$CO_2H$), 2.37 (t, 2H, $CH_2$—S), 5.13 (s, 1H, CH—Ph), 7.20–7.44 (m,10H, aromatic H).

(N-Methyl-N'-methyl-3,6,9-trioxa-1,11-diaminoundecane)-11-(diphenylmethylthiol-undecanamide

To a solution of diphenylundecanoic amine (700 mg, 1.82 mmol) and bisdimethylamino-tetraethyleneglycol diamine (2.0 g, 9.1 mmol) in dichloromethane (7 ml). DCC (565 mg, 2.74 mmol) and DMAP (75 mg, 0.62 mmol) dissolved in dichloromethane (3 ml) was added. The mixture stirred at RT under nitrogen for 48 h. The solvent evaporated and the residue was purified by chromatography (dichloromethane:MeOH 90:10 to remove urea salt and dichloromethane:MeOH:$NH_3$ 80:20:2) to give the product (390 mg, 37%) as a colourless liquid. (Found C, H, N $C_{34}H_{54}N_2O_4S$ requires C, 69.58; H, 9.27; N, 4.77) ms (EI) 587.

$^1$H nmr ($CDCl_3$)1.22 (m, 12H, $CH_2$), 1.58 (m, 4H, $CH_2$), 2.38 (t, 2H, $CH_2$—$CO_2H$), 2.49 (t, 2H, $CH_2$—S), 2.50 (s, 3H, $NCH_3$—$CH_2$), 2.83 (t, 2H, $CH_2$—$NCH_3$), 2.93 ((s) 3.04 (s), 3H, $NCH_3$—CO), 3.54–3.64 (m, 14H, $CH_2$—O), 5.13 (s, 1H, CH—Ph), 7.20–7.43 (m,10H, aromatic H).

((N-Methyl-N'-methyl-3.6.9-trioxa-1,11-diaminoundecane)-11-(diphenylmethylthio)-undecanamide(N-methyl-N'-methyl-3,6,9-trioxa-1, 11-diaminoundecane)succinamide)hemisuccinamide To a solution of (N-methyl-N'-methyl-3,6,9-trioxa-1,11-diaminoundecane)-11-(diphenylmethylthio)-undecanamide (200 mg, 0.34 mmol) and bis-(N-methyl-N'-methyl-3,6,9-trioxa-1,11-diaminoundecane)hemisuccinamide (572 mg, 1.36 mmol) in dichloromethane (10 ml), DCC (110 mg, 0.53 mmol) and DMAP (13 mg, 0.10 mmol) dissolved in dichloromethane (4 ml) was added. The mixture stirred at RT under nitrogen for 24 h. The white ppt. Of the urea was filtered and washed with dichloromethane. More dichloromethane (50 ml) was added and washed with water (2×30 ml), brine (30 ml), dried and evaporated. The residue was then purified by hplc(4% MeOH, 0.5% acetic acid in dichloromethane) on a semi prep column with retention time (29 min) to give the product (160 mg,47%) a colourless liquid. (Found C, H, N $C_{52}H_{84}N_4O_{12}S$ requires C,; H,; N,) ms (ESI) 989 and M+Na 1012.

$^1$H nmr ($CDCl_3$) 1.25 (m, 12H, $CH_2$), 1.57 (m, 4H, $CH_2$), 2.33 (m, 2H, $CH_2$—$CO_2H$), 2.37 (m, 2H, $CH_2$—S), 2.61–2.67 (m, 8H, CO—$CH_2$—$CH_2$—CO), 2.95, 2.97,3.06, 3.09, 3.11 ((s) 15H, $NCH_3$—CO), 3.55–3.61 (m, 32H, $CH_2$—O), 5.14 (s, 1H, CH—Ph), 7.16–7.41 (m,10H, aromatic H).

(((N-Methyl-N'-methyl-3,6,9-trioxa-1,11-diaminoundecane)-11-(diphenylmethylthio)-undecanamide(N-methyl-N'-methyl-3,6,9-trioxa-1,11-diaminoundecane)succinamide)N-methylphytanamine)succinamide

To a solution of (N-methyl-N'-methyl-3,6,9-trioxa-1,11-diaminoundecane)-11-(diphenylmethylthio)-undecanamide (100 mg, 0.17 mmol) and (N-methylphytanamine(N-methyl-N'-methyl-3,6,9-trioxa-1,11-diaminoundecane)succinamide)hemisuccinamide (160 mg, 0.22 mmol) in dichloromethane (10 mL), DCC (52 mg, 0.25 mmol) and DMAP (6 mg, 0.05 mmol) dissolved in dichloromethane (3 ml) was added. The mixture stirred at RT under nitrogen for 24 h. The solvent evaporated and the residue was purified by chromatography (DCM:MeOH 95:5) to give the product (180 mg, 83%) as a colourless liquid. (Found C, H, N $C_{73}H_{127}N_5O_{11}S$ requires C,; H,; N,) ms (ESI) 1282 and M+Na 1305.

$^1$H nmr (CDCl$_3$))0.82–1.25 (m, 55H, CH$_2$), 1.59 (m, 4H, CH$_2$), 2.33 (t, 2H, CH$_2$—CO$_2$H), 2.37 (t, 2H, CH$_2$—S), 2.65–2.68 (m, 8H, CO—CH$_2$—CH$_2$—CO), 2.89, 2.95, 2.99, 3.04, 3.09 ((s) 15H, NCH$_3$—CO), 3.54–3.64 (m, 34H, CH$_2$—O), 5.13 (s, 1H, CH—Ph), 7.20–7.43 (m,10H, aromatic H).

(((N-Methyl-N'-methyl-3,6,9-trioxa-1,11-diaminoundecane)-11-thioundecanamide(N-methyl-N'-methyl-3,6,9-trioxa-1,11-diaminoundecane)succinamide)N-methylphytanamine)succinamide A solution of (((N-methyl-N'-methyl-3,6,9-trioxa-1,11-diaminoundecane)-11-(diphenylmethylthio)-undecanamide (N-methyl-N'-methyl-3,6,9-trioxa-1,11-diaminoundecane) succinamide)N-methylphytanamine)succinamide (100 mg, 0.78 mmol) and phenol (144 mg) in trifluoroacetic acid (1 ml), was stirred at RT under nitrogen. After 6 h (the hplc indicated the disappearance of the starting material) the trifluoroacetic acid was removed under high vacuum and the residue was purified by hplc (dichloromethane:methanol 93:7) to give a single peak of the product (39 mg, 45%) a colourless liquid. (Found C, H, N $C_{60}H_{117}N_5O_{11}S$ requires C,; H,; N,) ms (CI) 1117 (M+1)

$^1$H nmr (CDCl$_3$) 82–1.25 (m, 55H, CH$_2$), 1.59 (m, 4H, CH$_2$), 2.35 (m, 2H, CH$_2$—CO$_2$H), 2.60 (m, 2H, CH$_2$—S), 2.65–2.68 (m, 8H, CO—CH$_2$—CH$_2$—CO), 2.89, 2.95, 2.99, 3.04, 3.09 ((s) 15H, NCH$_3$—CO), 3.54–3,64 (m, 34H, CH$_2$—O).

(((N-Methyl-N'-methyl-3,6,9-trioxa-1,11-diaminoundecane)-11-(diphenylmethylthio)-undecanamide(N-methyl-N-methyl-3,6,9-trioxa-1,11-diaminoundecane)succinamide)gramicidin-lysine)succinamide To a solution of ((N-methyl-N'-methyl-3,6,9-trioxa-1,11-diammnoundecane)-11-(diphenylmethylthio)-undecanamide(N-methyl-N'-methyl-3,6,9-trioxa-1,11-diaminoundecane)succinamide)hemisuccinamide (40 mg, 0.04 mmol) and gramicidin lysine (30 mg, 0.02 mmol) in dichloromethane (3 ml), DCC (10.5 mg, 0.05 mmol) and DMAP (6 mg, 0.05 mmol) dissolved in dichloromethane (1 ml) was added. Pyridine (0.5 ml) was added to dissolve the suspension. The mixture stirred at RT under nitrogen for 72 h. The solvent evaporated and the residue purified by reverse phase hplc gradients (A: water B: methanol 50 to 70 to 100 over 60 min) to give the product (8 mg,17%) as fraction 4 with retention time 52 min as white precipitate. ms (ESI) M+Na 2961.

(((N-Methyl-N'-methyl-3,6,9-trioxa-1,11-diaminoundecane)-11-thio-undecanamide(N-methyl-N'-methyl-3,6,9-trioxa-1,11-diaminoundecane)succinamide)gramicidin-lysine)succinamide A solution of diphenyl undecanoicTEG-Succ-TEG-Succ-gALys (9 mg, 0.003 mmol) and phenol (60 mg) in trifluoroacetic acid (0.4 ml), was stirred, at RT under nitrogen. After 3 h (the hplc indicated the disappearance of the starting material) the trifluoroacetic acid was removed under high vacuum and the residue was purified by hplc (gradients (A: water B: methanol 50 to 70 to 100 over 30 min) to give the product (1.4 mg, 18%) with retention time 27.53 min as white precipitate. ms (ESI) M+Na 2795.

Bis-dimethylamino Membrane Spanning Lipid (MSL dimethyldiamine)

A solution of the $C_{38}$-dimesylate (750 mg, 0.5 mmol) was added to anhydrous methylamine (19 mL) at −12° C. The reaction mixture, in a pressure tube, was allowed to warm to room temperature and was gently stirred for 48 h. The excess methylamine was removed and the residue was stirred with excess anhydrous potassium carbonate in dichloromethane for 3 h. The mixture was filtered through barium carbonate and the solvent removed to give a waxy solid. Chromatography on silica gel with 1% ammonia and 4% methanol in dichloromethane followed by 1% ammonia and 8% methanol in dichloromethane as eluent gave the $C_{38}$-diamine (423 mg, 62%) as a white waxy solid.

$^1$H nmr (CDCl$_3$) 0.80–1.89 (130H, m, aliphatics), 2.49 (6H, s, NMe), 2.76 (4H, m, CH$_2$N), 3.36–3.78 (14H, m, OCH and OCH$_2$), 3.98 (4H, t, $^3$J 6.5 Hz, CH$_2$OAr), 6.95 and 7.46 (8H, AA'BB', biphenyl). $n_1/\theta$ 687.5 (M$^{2+}$) (M$^+$ requires 1374.3).

EXAMPLE 1

Bilayer: Comparison of Bottom Layer

A freshly prepared evaporated gold thin film (1000 A) on glass with chromium under-layer (50 A) was clamped in a containment vessel. Ten microliters of ethanol solution of compound DLP 1 mM was added into the vessel thus covering the gold electrode. After one hour the electrode was washed with ethanol and dried using nitrogen gas. Five microliters of PC lipid mixture in ethanol with ionophore valinomycin (200:1) was added to the electrode. The electrode was rinsed then three times with 0.5 mL of 0.1M saline solution. Impedance spectra were obtained before and after 0.1M potassium challenge.

Another freshly prepared evaporated gold thin film (1000 A) on glass with chromium under-layer (50 A) was clamped in a containment vessel. Ten microliters of ethanol solution of compound B 1 mM was added into the vessel thus covering the gold electrode. After one hour the electrode was washed with ethanol and dried using nitrogen gas. Five microliters of PC lipid mixture in ethanol with ionophore valynomicin (200:1) was added to the electrode. The electrode was rinsed then three times with 0.5 mL of 0.1M saline solution. Impedance spectra were obtained before and after 0.1M potassium challenge.

Yet another freshly prepared evaporated gold thin film (1000 A) on glass with chromium under-layer (50 A) was clamped in a containment vessel. Ten microliters of ethanol solution of compound L 1 mM was added into the vessel thus covering the gold electrode. After one hour the electrode was washed with ethanol and dried using nitrogen gas. Five microliters of PC lipid mixture in ethanol with ionophore valynomicin (200:1) was added to the electrode. The electrode was rinsed then three times with 0.5 mL of 0.1M saline solution. Impedance spectra were obtained before and after 0.1M potassium challenge.

Impedance at 1 kHz. 1 Hz, phase shift minimum and frequency at phase shift minimum for DLP, DLP-C11 and DLP-C16 based bilayers: after KCl challenge are shown in the Table below.

|  | $[Z]_.$ kOhm 1 kHz | | $[Z]_.$ kOhm 1 Hz | | min psi deg | | min frequency Hz |
|---|---|---|---|---|---|---|---|
| DLP | 1.86 | 3.5% | 158 | 12% | 39 | 4% | 10–20 |
| DLP-C11 | 1.94 | 4% | 338 | 7% | 50 | 3% | 10 |
| DLP-C16 | 2.34 | 4% | 497 | 22% | 57 | 6% | 10 |

Impedances at 1 kHz and 1 Hz and phase shift minimum increase when the monolayer thickness increases from BnDS to C11 to C16 molecules. The frequency minimum on the other hand is only weakly affected by the change.

EXAMPLE 2

Stability: Monolayers
2.1 Stability of C11 and C16 DLP and DLP in H$_2$O at 50° C. Using X-ray Photoelectron Spectroscopy (XPS)
Method A freshly prepared evaporated gold thin film (1000 A) on glass with chromium under-layer (50 A) was immersed into a vessel containing ethanolic solution 1 mM of compound the vessel thus covering the gold electrode. After one hour the electrode was washed with ethanol and dried using nitrogen gas and measured with XPS. The samples were immersed in deionised H$_2$O for 1 hr at 50° C. and measured again by XPS. The regions of interest were C1s, O1s and Au 4f. The values quoted below are the average of two measurements on one sample.

TABLE 1

Carbon and Oxygen, % (Integrity of monolayer)

| Monolayer | C % before | after | O % before | after | ratio (C/O) before | after |
|---|---|---|---|---|---|---|
| C16-S-S-C16-DLP | 78.4 | 78.9 | 21.6 | 21.1 | 3.63 | 3.73 |
| C11-S-S-C11-DLP | 77.7 | 77.7 | 22.3 | 22.3 | 3.48 | 3.48 |
| DLP (standard) | 75 | 76 | 25 | 24 | 3 | 3.16 |

TABLE 2

Carbon and Au % (surface coverage)

| Monolayer | C (area) before | after | Au (area) before | after | Au/C ratio before | after |
|---|---|---|---|---|---|---|
| C16-S-S-C16-DLP | 5377 | 6012 | 20848 | 22826 | 3.88 | 3.80 |
| C11-S-S-C11-DLP | 5511 | 5637 | 24114 | 26751 | 4.38 | 4.74 |
| DLP (standard) | 5454 | 5319 | 47854 | 56988 | 8.77 | 10.7 |

TABLE 3

O %:Au % (surface coverage)

| Monolayer | O (area) before | after | Au (area) before | after | Au/O ratio before | after |
|---|---|---|---|---|---|---|
| C16-S-S-C16-DLP | 4015 | 4073 | 20848 | 22826 | 5.20 | 5.59 |
| C11-S-S-C11-DLP | 4012 | 4103 | 24114 | 26751 | 6.0 | 6.52 |
| DLP (standard) | 4635 | 4066 | 47854 | 56988 | 10.3 | 14.0 |

Table 1 shows that the ratio between the carbon and oxygen content of various DLP's monolayers. The variation is within the experimental error indicating that the molecules did not disintegrate and if any desorption occurred it would be take place in the form of disulfide bond breaking from the Au surface.

Table 2. shows a comparison of carbon and Au content of various DLP's monolayers before and after 50° C. ethanol immersion. The result show that C16-DLP is the least effected by immersion of $H_2O$ at 50° C., C11-DLP is effected slightly and the greatest effect seen with DLP.

Table 3. shows a comparison of oxygen content of various DLP's monolayers before and after 50° C. ethanol immersion. The result show that C16-DLP is the least effected by immersion of $H_2O$ at 50° C., C11-DLP is effected slightly and the greatest effect seen with DLP. This suggests that the further the monolayer (i.e. the longer molecule) is from the gold surface the more protected it remains.

2.2 Stability of C11 and C16 DLP and DLP in Ethanol at 50° C. Using XPS

Method

Au thin film were sputtered onto Si substrate with Ti interlayer. The samples were immersed for 1 hr at room temperature and measured with XPS. Then the samples were immersed in ethanol for 1 hr at 50° C. and measured again by XPS. The regions of interest were C1s, O1s and Au 4f. The values quoted below are the average of two measurements on one sample.

TABLE 4

Monolayer composition and Au percentage detected.

| Monolayer | C % before | after | O % before | after | Au % before | after |
|---|---|---|---|---|---|---|
| C16-S-S-C16-DLP | 67.7 | 67.4 | 22.2 | 22.0 | 10.1 | 10.6 |
| C11-S-S-C11-DLP | 64.2 | 64.4 | 20.5 | 19.1 | 15.3 | 16.5 |
| DLP (standard) | 65.0 | 63 | 20.0 | 18.9 | 15.0 | 18.1 |
| C18-thiol | 54.4 | 51.3 | — | — | 45.6 | 48.7 |

Table 4 shows a trend where the sample immersed in ethanol at 50° C. the Au percentage increased indicating a desorption of the outer layer. Also, this effect appeared to be dependent on the length of the molecules, the longer the molecules the less the increase in Au percentage is observed.

TABLE 5

Carbon and Oxygen percentage of DLP's monolayers

| Monolayer | C % before/ after | | O % before/ after | | Au % before/ after | |
|---|---|---|---|---|---|---|
| C16-S-S-C16-DLP | 77.8 | 78 | 22.2 | 22.0 | 3.5 | 3.55 |
| C11-S-S-C11-DLP | 75.8 | 77.1 | 24.2 | 22.9 | 3.13 | 3.37 |
| DLP (standard) | 76.5 | 76.9 | 23.5 | 23.1 | 3.26 | 3.33 |

The ratio of carbon to oxygen is a measure of monolayer integrity. The ratio for each of the monolayer do not changes significantly suggesting that the molecules do not disintegrate.

TABLE 6

Carbon and gold of DLP's monolayers (surface coverage)

| Monolayer | C (area) before | after | Au (area) before | after | Au/C ratio before | after |
|---|---|---|---|---|---|---|
| C16-S-S-C16-DLP | 5948 | 5807 | 22849 | 23385 | 3.84 | 4.02 |
| C11-S-S-C11-DLP | 5216 | 5163 | 24641 | 28138 | 4.72 | 5.5 |
| DLP (standard) | 1766 | 812 | 8176 | 4620 | 4.63 | 5.69 |
| C18-thiol | 950 | 534 | 16017 | 10473 | 16.9 | 19.6 |

TABLE 7

Oxygen and gold of DLP's monolayers (surface coverage)

| Monolayer | O (intensity) before | after | Au (intensity) before | after | Au/O ratio before | after |
|---|---|---|---|---|---|---|
| C16-S-S-C16-DLP | 4331 | 4165 | 22849 | 23385 | 5.28 | 5.61 |
| C11-S-S-C11-DLP | 4212 | 4115 | 24641 | 28138 | 5.85 | 6.84 |
| DLP (standard) | 1384 | 755 | 8176 | 4620 | 5.91 | 6.2 |

EXAMPLE 3

Bilayer: Transient

A freshly prepared evaporated gold thin film (1000 A) on glass with chromium under-layer (50 A) was clamped in a containment vessel. Ten microliters of ethanol solution of compound DLP 1 mM was added into the vessel thus covering the gold electrode. After one hour the electrode was washed with ethanol and dried using nitrogen gas.

Five microliters of PC lipid mixture in ethanol with ionophore valynomicin (200:1)was added to the electrode. The electrode was rinsed then three times with 0.5 mL of 0.1M saline solution. A transient technique was used to measure sensor response.

A train of potential pulses was applied to the electrode using a commercial potentiostat, EG&G 263M Princeton with AMLAB computer control data acquisition system (pulse duration 50 msec, delay between pulses 950 msec). The currect response of the system was measured before and after 0.1M potassium challenge. The shape of the current response changes upon changes in the concentration of potassium ions. The current can be fitted using two exponential function with time constants tau1 and tau2. The electrolyte concentration can be correlated with one of the time constant that is related with the membrane conductance.

EXAMPLE 4

Ferritin Gating Experiments

Aim

To demonstrate that a ferritin gating response can be achieved with membrane systems incorporating C11-amide gAYY.

Method:
1st layer solutions:

i) AM300

| | | |
|---|---|---|
| DLP | 10 mM | 1500 µL |
| MSLOH | 1 mM | 225 µL |
| MAAD | 10 mM | 750 µL |
| MSL4XB | 0.1 mM | 11.25 µL |
| gAYY | 0.01 mg/mL | 579 µL |
| + 48.9 mL EtOH | | | ii) 2,000:1, C11-DLP/C11-amide gAYY

| | | |
|---|---|---|
| DLP-C11 | 10 mM | 25 µL |
| $HS(CH_2)_{10}CO_2H$ | 1 mM | 125 µL |
| C11-amide gAYY | 3.61 µM | 34.7 µL |
| + 815.3 µL EtOH | | | iii) 5,000:1, C11-DLP/C11-amide gAYY;

| | | |
|---|---|---|
| DLP-C11 | 10 mM | 25 µL |
| $HS(CH_2)_{10}CO_2H$ | 1 mM | 125 µL |
| C11-amide gAYY | 3.61 µM | 138.6 µL |
| + 711.4 µL EtOH | | |

Standard, Hand Assembled Blocks were Used $1^{st}$ Layer Formation

Fresh slides were obtained from the evaporator and used immediately. Slides were assembled in blocks and to each cell 40 µL of $1^{st}$ layer solution added.

Blocks were incubated with $1^{st}$ layer solution for ~2–3 hours at room temperature, whereupon excess solution was removed, and each cell rinsed thoroughly with ethanol from a wash bottle. Residual ethanol was removed by vigorous shaking and blocks inverted and air-dried.

$2^{nd}$ Layer Formation $5\times10^4/4$ gA-5XB conducting membranes were assembled using 10 mM DPEPC:GDPE 7:3. After assembly membranes were challenged with;

i) 5 µL, 0.1 mg/mL Streptavidin, PBS wash(3×)

ii) 5 µL, 0.05 mg/mL anti-Ferritin Fab', PBS wash (3×)

ii) 100 µL, 100 pM Ferritin

N.B.: 2 different substrates were used; (i.e. deposition process—evaporation)

i) polycarbonate/Cr+Au ii) glass/Cr+Au

TABLE 1

Comparison of Ferritin Gating responses (50 pM final conc.)

| $1^{st}$ layer | No. Cells | 1 Hz Intercept [kHz] | | 1 kHz Intercept [kHz] | |
|---|---|---|---|---|---|
| | | Av. | C.V. | Av. | C.V. |
| AM300 | 4 | 140 | 3.6 | 1.8 | 4.8 |
| 2,000:1 | 5 | 502 | 10.7 | 2 | 11 |
| 5,000:1 | 6 | 416 | 5 | 2 | 5.6 |
| AM300 | 7 | 118 | 23.8 | 1.4 | 2.7 |
| 2,000:1 | 14 | 446 | 18.8 | 2.1 | 7.7 |
| 5,000:1 | 6 | 453 | 3.4 | 1.7 | 5.2 |
| AM300 | 3 | 149 | 3.9 | 1.8 | 3.9 |
| 2,000:1 | 15 | 457 | 2.3 | 1.9 | 3.4 |

| $1^{st}$ layer | Freq. Min. Phase (Hv) | | NMS (·/ks) | |
|---|---|---|---|---|
| | Av. | C.V. | Av. | C.V. |
| AM300 | 18. | 20.1 | 1.231 | 9.9 |
| 2,000:1 | 413 | 100.6 | 0.651 | 22.4 |
| 5,000:1 | 37 | 33 | 0.689 | 24.1 |

TABLE 1-continued

Comparison of Ferritin Gating responses (50 pM final conc.)

| | | | | |
|---|---|---|---|---|
| AM300 | 43.7 | 10.1 | 1.671 | 7.7 |
| 2,000:1 | 23.9 | 16.1 | 1.325 | 17.2 |
| 5,000:1 | 16.7 | 16.3 | 1.287 | 14.8 |
| AM300 | 31.8 | 8.1 | 0.976 | 5.8 |
| 2,000:1 | 42.3 | 12.4 | 0.581 | 7 |

| $1^{st}$ layer | Tau (sec.) | | % Gating | |
|---|---|---|---|---|
| | Av. | C.V. | Av. | C.V. |
| AM300 | 528 | 14.7 | 52 | 3.9 |
| 2,000:1 | 795 | 7.6 | 51 | 12.4 |
| 5,000:1 | 785 | 26 | 42 | 0.5 |
| AM300 | 247 | 10.4 | 43 | 9.5 |
| 2,000:1 | 242 | 13.3 | 36.5 | 14 |
| 5,000:1 | 290 | 9.1 | 40 | 8.6 |
| AM300 | 517 | 8 | 49.3 | 3.3 |
| 2,000:1 | 1391 | 16 | 53 | 14.5 |

Conclusion

A ferritin gating response can be elicited from membranes assembled with C11-amide modified gAYY. From the 3 different data sets, the magnitude of the gating response is comparable to the standard AM300 system, however there is some variation in the speed of response and initial membrane conductivity.

EXAMPLE 5

Stability Trials Testing C11-amide gAYY i) "AM300"

| | | |
|---|---|---|
| DLP | 10 mM | 1500 µL |
| MSLOH | 1 mM | 225 µL |
| MAAD | 10 mM | 750 µL |
| MSL4XB | 0.1 mM | 11.25 µL |
| gAYY | 0.01 mg/mL | 579 µL |
| + 807.5 µL EtOH | | | ii) 2,000:1 DLP-C11/C11-ester gAYY;

| | | |
|---|---|---|
| DLP-C11 | 10 mM | 25 µL |
| $HS(CH_2)_{10}CO_2H$ | 1 mM | 125 µL |
| C11-ester gAYY | 0.01 mg/mL | 42.3 µL |
| + 46.9 mL EtOH | | | iii) 5,000:1 C11DLP/C11-amide gAYY;

| | | |
|---|---|---|
| DLP-C11 | 10 mM | 25 µL |
| $HS(CH_2)_{10}CO_2H$ | 1 mM | 125 µL |
| C11-amide gAYY | 3.61 µM | 138.6 µL |
| + 711.4 µL EtOH | | |

Manual assembled blocks were used.

Substrate polycarbonate/Cr+Au (Evaporated)

$1^{st}$ Layer Formation

Fresh slides were obtained from the evaporator and used immediately Slides were assembled in blocks and to each cell 40 µL of $1^{st}$ layer solution added.

Blocks were incubated with $1^{st}$ layer solution for ~2–3 hours at room temperature, whereupon excess solution was removed, and each cell rinsed thoroughly with ethanol from a wash bottle. Residual ethanol was removed by vigorous shaking and blocks inverted and air-dried.

$2^{nd}$ Layer Formation

Sealed, non-conducting membranes were prepared using 10 mM DPEPC/GDPE 7:3.

Blocks were stored at room temperature in PBS and the impedance measured at 0.1 Hz at periodic intervals, Results Averaged Impedance Plots The averaged impedance plots of the test system (i.e. with the inclusion of C11-amide gAYY, 5,000:1) and 2 controls; AM300 and a membrane system with C11-ester analogues only were determined. These membranes were stored in PBS at room temperature, with the first 7 days of data being shown.

The AM300 showed a rapid increase in membrane leakage after 7 days storage. In comparison, when both the C11-SH passivity layer and amide linkages are incorporated into the tethered gramicidin component (i.e. C11-amide gAYY), the membrane remained well sealed, with no change in stability after 7 days storage.

Membranes assembled from C11-ester analogues only showed improvement over AM300 but were not as stable as the C11-amide gAYY. Similar results were obtained after 3 weeks and 5 weeks storage.

CONCLUSION

It has been shown that a stable, fully hydrated bilayer membrane can be achieved by improving the chemical stability within the reservoir region When membranes are assembled with a C11-amide modified tethered gramicidin, membranes are stable for at least 5 weeks at room temperature with no significant loss of sealing ability.

The inclusion of a passivity layer (C11-SH tether) improves the Au—S attachment, while the introduction of amide linkages are more resistant to hydrolysis. These improvements minimise the ability of the tethered gramicidin to detach from the substrate surface, allowing it to transfer between membrane layers.

This result represents the most significant advance as it overcomes the rapid degradation/leakage associated with the short term stability of current membrane based biosensor systems.

The membrane stability with this new architecture may be further enhanced by minimising degradation due to mechanical leakage. The use of a slide laminate will help to define the cell area in a more controlled manner and reduce the likelihood of membrane leakage underneath the teflon inserts of the current block assembly.

It is also important to note that the membrane stability achieved is in the absence of any membrane spanning component in the bilayer. Further improvements in stability would most likely be achieved with the inclusion of a transmembrane lipid.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A membrane based biosensor, the biosensor including an electrode, a passivating layer bound to the electrode, a lipid membrane incorporating ionophores, the conductivity of the membrane being dependent on the presence or absence of an analyte, an ionic reservoir between the membrane and the passivating layer, and reservoir spanning molecules spanning the ionic reservoir the molecules being covalently attached at one end to the membrane and at the other to the passivating layer.

2. A membrane based biosensor as claimed in claim 1 in which the biosensor includes a plurality molecules of following general structure;

in which:

A is a hydrophobic group of between 2–50 methylene units in length;

B is a group which spans the ionic reservoir;

C is a group capable of hydrogen bonding, forming van der Waal's interactions, ionic bonding or covalent bonding with other molecules within the passivating layer; and D is a group which binds to the conducting substrate.

3. A membrane based biosensor as claimed in claim 2 in which A is a hydrocarbon group of between 2–50 methylene units long, a phytanyl group, an unsaturated hydrocarbon of between 2–50 methylene groups long, a membrane spanning lipid, an archaebacterial lipid, a lipid hydrocarbon group, or a gramicidin derivative.

4. A membrane based biosensor as claimed in claim 3 in which A is a hydrocarbon group or an unsaturated hydrocarbon group of between 8–26 methylene units long or a gramicidin derivative.

5. A membrane based biosensor as claimed in claim 2 in which B is an oligoethylene glycol of between 4 to 20 ethylene glycol units long.

6. A membrane based biosensor as claimed in claim 2 in which B is repeating subunits of oligoethylene glycol of between 2 and 6 ethylene glycol units, the subunits being linked together via ester, amide or other linkages.

7. A membrane based biosensor as claimed in claim 6 in which linkages do not promote hydrogen bonding between the groups spanning the reservoir.

8. A membrane based biosensor as claimed in claim 6 in which the linkages are tertiary amides.

9. A membrane based biosensor as claimed in claim 2 in which C includes a secondary amide capable of hydrogen bonding with other amides; a hydrocarbon group capable of forming van der Waals interactions with other hydrocarbon groups, or a polymerisable group.

10. A membrane based biosensor as claimed in claim 9 in which C is a saturated hydrocarbon group of between 2 to 50 methylene units long.

11. A membrane based biosensor as claimed in claim 10 in which C is a saturated hydrocarbon group of between 8 to 30 methylene units long.

12. A membrane based biosensor as claimed in claim 2 in which D is a thiol, disulfide, sulfide, phosphine, silane or carboxylate.

13. A membrane based biosensor as claimed in claim 12 in which C is a saturated hydrocarbon group of between 2 to 50 methylene units long.

14. A membrane based biosensor as claimed in claim 13 in which C is a saturated hydrocarbon group of between 8 to 30 methylene units long.

15. A membrane based biosensor as claimed in claim 2 in which the molecule A—B—C—D is of the formula:

where:

n=8 to 16 m=1 to 10 p=1 to 10 k=0 to 10

R, $R_1$, $R_2$, $R_3$, $R_4$=independently H, methyl, ethyl

L=hydrocarbon such as a phytanyl chain, or other lipidic hydrocarbon

P=a thiol disulfide, sulfide, or other group for attaching to metal surfaces such as gold, platinum, palladium, silver etc; or a silane or alkoxy silane or chloro silane for attaching to silica or metal oxide.

16. A membrane based biosensor as claimed in claim 1 in which the biosensor includes a plurality of molecules of the following structure:

A—B—(C—D)$_n$ in which:

A and B are as defined in claim 1;

C is a group capable of hydrogen bonding, forming van der Waal's interactions, ionic bonding or covalent bonding with other molecules within the passivating layer;

D is a group which binds to the conducting substrate; and n is at least 2.

17. A membrane based biosensor as claimed in claim 16 in which C includes a secondary amide capable of hydrogen bonding with other amides; a hydrocarbon group capable of forming van der Waals interactions with other hydrocarbon groups, or a polymerisable group.

18. A membrane based biosensor as claimed in claim 16 in which D is a thiol, disulfide, sulfide, phosphine, silane or carboxylate.

19. A membrane based biosensor as claimed in claim 1 in which the passivating layer has reduced permeability towards water and towards ions thus protecting the surface of the conductive substrate from destabilising effects due to water or ions.

20. A membrane based biosensor as claimed in claim 1 in which the reservoir spanning molecules are attached to the passivating layer via an ester, ether or amide linkage.

21. A membrane based biosensor as claimed in claim 20 in which the reservoir spanning molecules are attached to the passivating layer via an amide linkage.

22. A membrane based biosensor as claimed in claim 21 in which the reservoir spanning molecules are attached to the passivating layer via a secondary amide.

23. A membrane based biosensor as claimed in claim 1 in which the reservoir spanning molecules are attached to the lipid membrane via an ester, ether or amide linkage.

24. A membrane based biosensor as claimed in claim 23 in which the reservoir spanning molecules are attached to the lipid membrane via an amide linkage.

25. A membrane based biosensor as claimed in claim 24 in which the reservoir spanning molecules are attached to the lipid membrane via a secondary amide.

* * * * *